United States Patent [19]
Okazaki

[11] Patent Number: 5,400,091
[45] Date of Patent: Mar. 21, 1995

[54] OPHTHALMIC INSTRUMENT

[75] Inventor: Yasuhiro Okazaki, Tokyo, Japan

[73] Assignee: Kabushiki Kaisha TOPCON, Tokyo, Japan

[21] Appl. No.: 33,550

[22] Filed: Mar. 18, 1993

[30] Foreign Application Priority Data

Mar. 19, 1992 [JP] Japan .................................. 4-063049

[51] Int. Cl.6 ......................... A61B 3/10; A61B 3/12; A61B 5/0205
[52] U.S. Cl. .................................... 351/205; 351/200; 128/670
[58] Field of Search ............... 351/205, 211, 221, 200, 351/246, 206; 128/745, 670, 676, 687; 354/62

[56] References Cited

U.S. PATENT DOCUMENTS

| 3,948,248 | 4/1976 | Zuckerman et al. | 128/662.01 |
| 5,031,632 | 7/1991 | Watanabe | 351/206 |
| 5,116,116 | 5/1992 | Aizu et al. | 351/221 |
| 5,141,302 | 8/1992 | Arai et al. | 351/205 |

Primary Examiner—William L. Sikes
Assistant Examiner—David R. Parsons
Attorney, Agent, or Firm—Finnegan, Henderson, Farabow, Garrett & Dunner

[57] ABSTRACT

An ophthalmic instrument provided with an eye fundus measuring portion 1 for finding a position of the eye fundus of a patient's eye includes a transducer 11 for outputting a heartbeat signal corresponding to the heartbeat of a patient, a vital signal generating circuit 13, a synchronizing circuit 14, and a timer 16 each for actuating the eye fundus measuring portion 1 synchronously with the heartbeat signal.

9 Claims, 4 Drawing Sheets

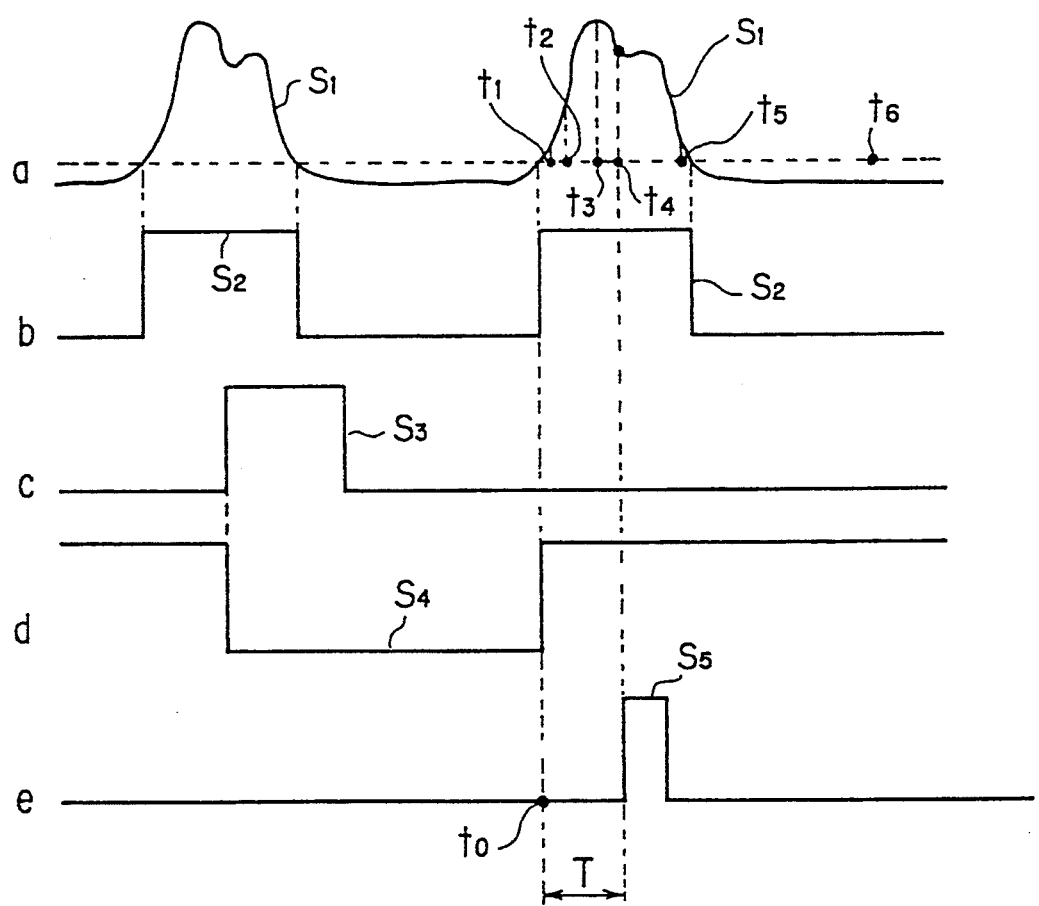

OPHTHALMIC INSTRUMENT

BACKGROUND OF THE INVENTION

1. Field of the Invention

This invention relates to an ophthalmic instrument provided with an eye fundus measuring portion for finding a position of the eye fundus of a patient's eye.

2. Description of the Prior Art

Heretofore, an ophthalmic instrument is known which is provided with an eye fundus measuring portion for finding a position of the eye fundus of a patient's eye.

To find the position of the eye fundus, this eye fundus measuring portion employs interference fringes which occur between low coherent light reflected from a reference mirror and low coherent light reflected from the eye fundus when positions of the reference mirror disposed in a reference optical path and the eye fundus coincide with each other. That is, the eye fundus measuring portion finds the position of the eye fundus such that alignment is first carried out, an optical system is then focused on the retina of the eye, the reference mirror is moved so as to discover a position at which interference fringes occur, and the position of the eye fundus is calculated from the interfering position of the reference mirror. Further, to measure an eye axis length (a length between the eye fundus and the cornea of the eye), a position of the cornea is found such that ring-shaped light is first projected onto the cornea, reflected light from the cornea is then received, and a corneal vertex position is calculated from the reflected light receiving position. Accordingly, the eye axis length is obtained as a difference between the positions of the eye fundus and the corneal vertex.

By the way, a plural number of light reflecting surfaces, such as the sclera, the choroid, and front and rear surfaces of the retina of the eye, line the eye fundus. In addition, the eye fundus is constantly moved by heartbeats of a patient, and thereby the eye axis length is changed.

Therefore, according to the heartbeats, the reflecting surface on which an optical system for projecting a laser beam onto the eye fundus is focused corresponds to any of the front and rear surfaces of the retina, the choroid, and the sclera of the eye. This results in a measurement error because the reflecting surface regarded as the eye fundus depends on operator's measuring timing.

For example, on the assumption that the retina is 0.2 mm thick, the difference between respective measured results obtained by light reflected from the front and rear surfaces of the retina is 0.2 mm. This difference cannot satisfy an accuracy 1/100 mm requisite for an instrument for measuring an eye axis length, and therefore the conventional measuring instrument could not accurately measure the eye axis length.

SUMMARY OF THE INVENTION

It is therefore an object of the invention to provide an ophthalmic instrument provided with a portion for accurately determining a position of the eye fundus regardless of the heartbeats of a patient.

The ophthalmic instrument according to the invention is characterized by a heartbeat detecting means for outputting a heartbeat signal corresponding to the heartbeat, and an actuating means for actuating the eye fundus measuring portion synchronously with the heartbeat signal.

BRIEF DESCRIPTION OF THE DRAWINGS

FIG. 4 is a time chart showing an output signal of each circuit.

DETAILED DESCRIPTION

The embodiment of an ophthalmic instrument according to the invention will be hereinafter described with reference to the appended drawings.

Figure 1:
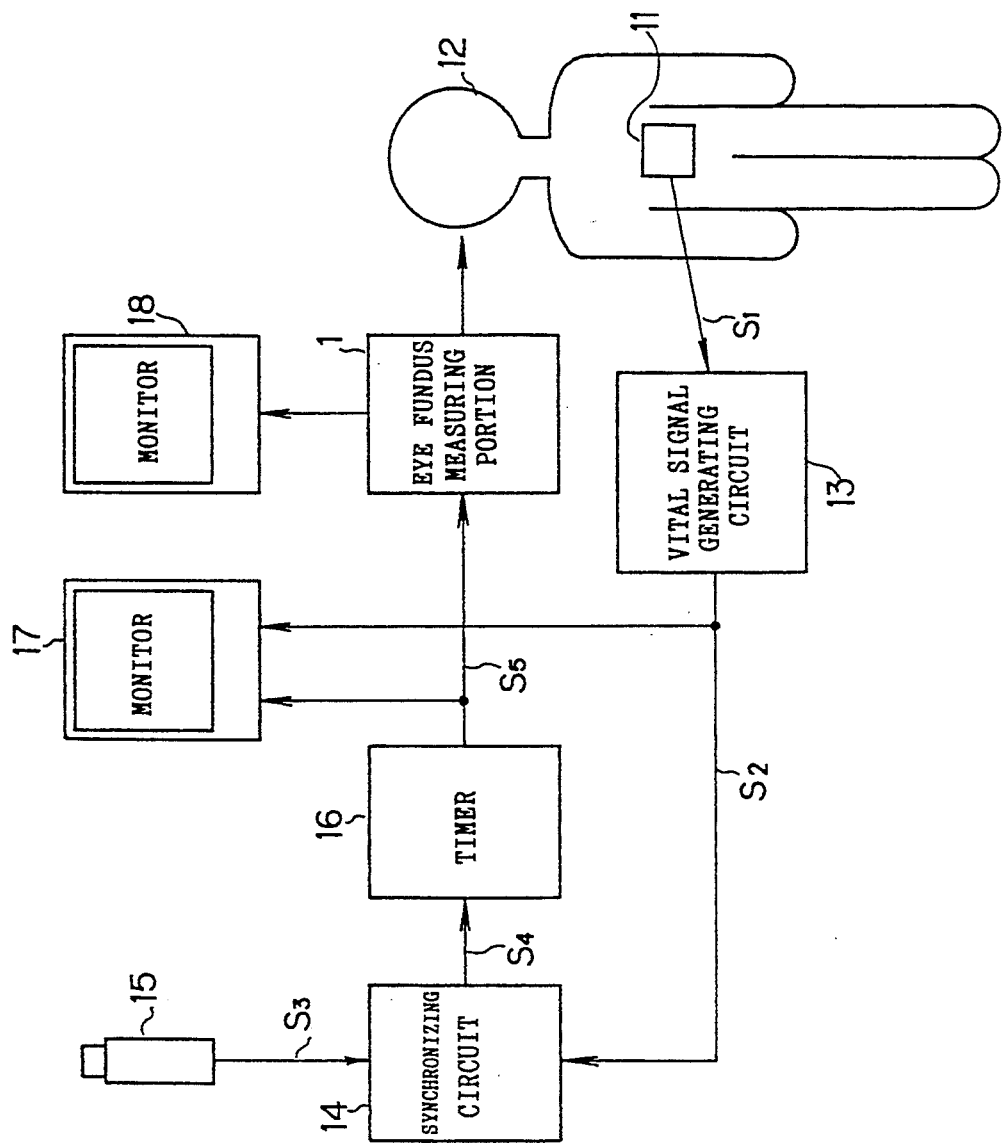
FIG. 1 is a block diagram showing an arrangement of an ophthalmic instrument according to the present invention.

Referring first to FIG. 1, an eye fundus measuring portion 1 serves to find a position of the eye fundus of a patient's eye E and measure an eye axis length when a synchronous signal is output from a timer 16 described hereinafter.

Figure 2:
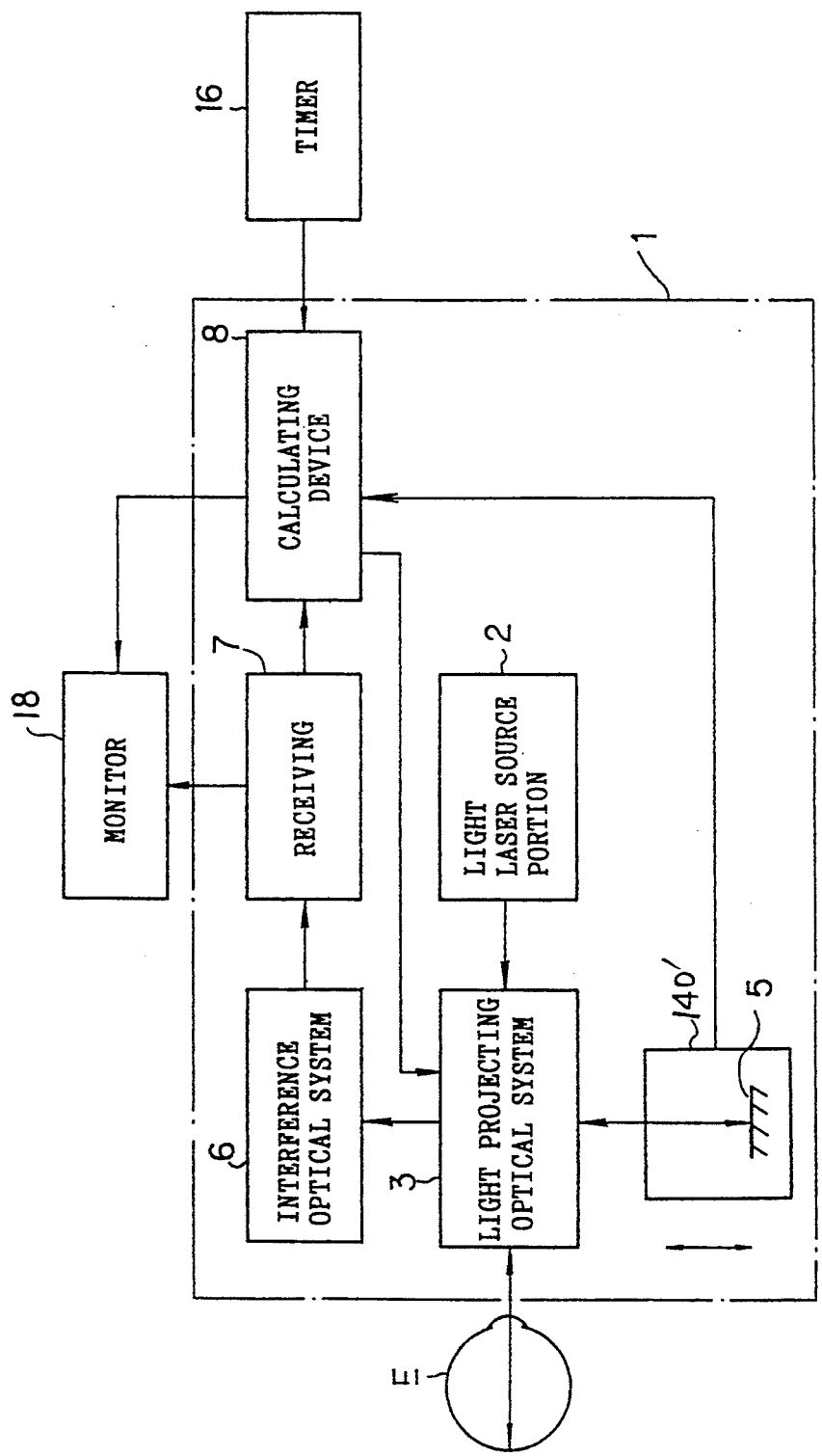
FIG. 2 is a block diagram showing an arrangement of an eye axis length measuring portion of the instrument according to the invention.

As shown in FIG. 2, the eye fundus measuring portion 1 includes a laser source 2 for emitting low coherent light having a short coherent length, a light projecting optical system 3 for projecting the light emitted by the laser source 2 onto the eye E, an interference optical system 6 for making interference between light reflected from the eye fundus and reference light reflected from a reference mirror 5 disposed in a reference optical path 140', a light receiving portion 7 for receiving interference light made by the interference optical system 6, a calculating device 8 for determining a position of the eye fundus from a position of the reference mirror 5 where interference fringes occur when the reference mirror 5 is moved and for calculating an eye axis length from the position of the eye fundus, and an aligning optical system (not shown).

Figure 3:
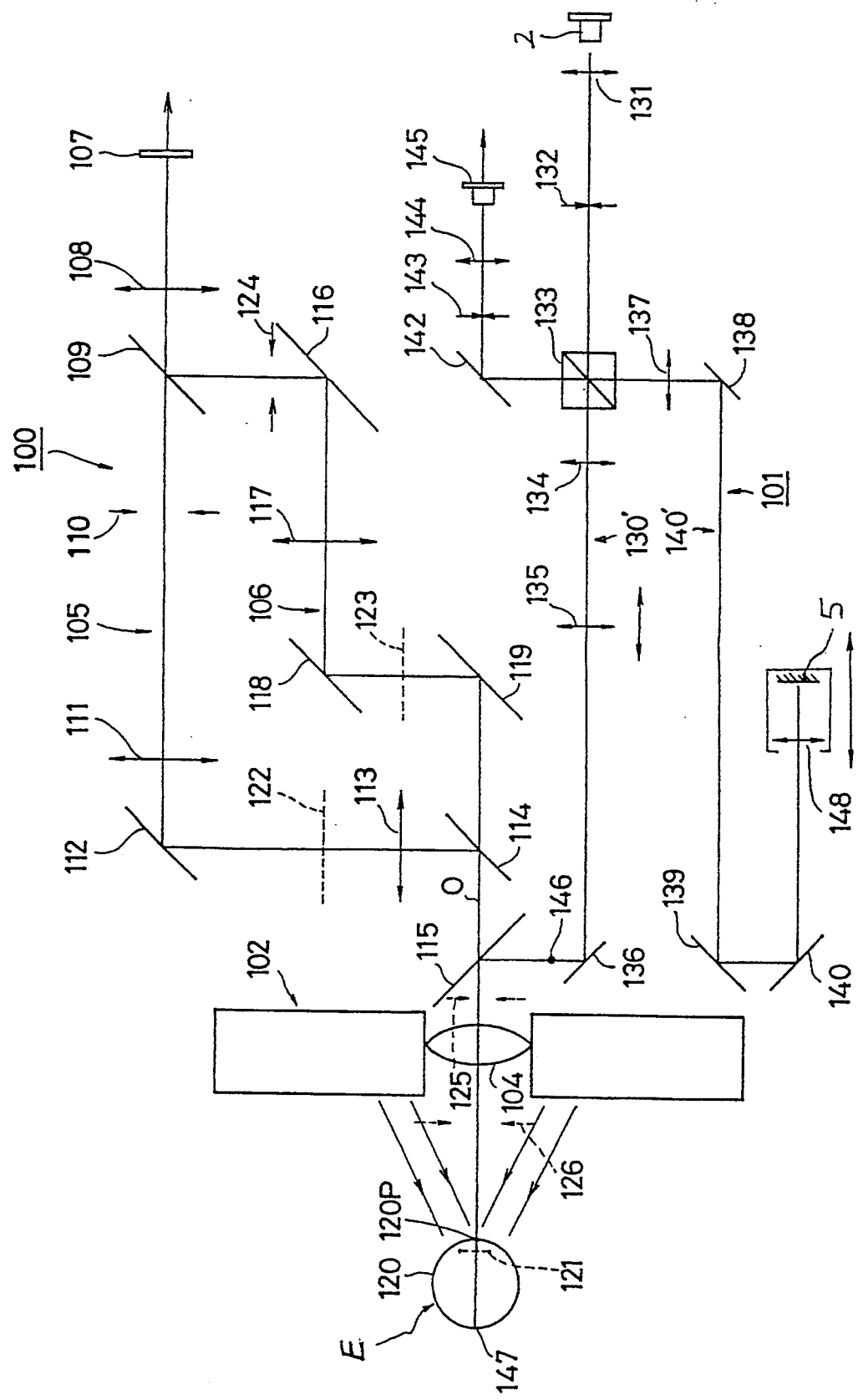
FIG. 3 is a view showing an optical system of an eye fundus measuring portion of the instrument according to the invention.

A description of the optical system of the eye fundus measuring portion 1 will be now given with reference to FIG. 3.

The reference numeral 100 denotes a cornea distance measuring system, 101 an eye fundus measuring optical system, 102 a ring-shaped light projecting portion for projecting light onto the cornea of the eye E, and 104 an objective lens. The cornea distance measuring system 100 includes first and second optical paths 105, 106. The first optical path 105 includes a two-dimensional image sensor 107, an image forming lens 108, a half mirror 109, a diaphragm 110, a lens 111, a total reflection mirror 112, a lens 113, a half mirror 114, a dichroic mirror 115, and an objective lens 104. The second optical path 106 includes a half mirror 116, a lens 117, total reflection mirrors 118 and 119, and a diaphragm 124.

The ring-shaped light projecting portion 102 includes a ring-shaped light source and a pattern plate (not shown). When this illuminating light is projected onto the eye E, a ring-shaped virtual image 121 is formed on the cornea 120 of the eye E. The dichroic mirror 115 serves to transmit the illuminating light and reflect a wavelength of a near infrared ray.

Reflected light from the cornea 120 is guided to the half mirror 114 through the objective lens 104 and the dichroic mirror 115 and branched to the first and second optical paths 105 and 106. The reflected light guided to the first optical path 105 is once imaged as a ring-shaped aerial image 122 through the lens 113 and then imaged as a ring-shaped image i2 (not shown) on the two-dimensional image sensor 107 via the total reflection mirror 112, the lens 111, the diaphragm 110, the half mirror 109, and the image forming lens 108.

On the other hand, the reflected light guided to the second optical path 106 is first reflected by the total reflection mirror 119, then once imaged as an aerial image 123 through the objective lens 104 and then imaged on the two-dimensional image sensor 107 as a ring-shaped image i1 (not shown) through the total reflection mirror 118, the lens 117, the half mirror 116, the diaphragm 124, the half mirror 109, and the image forming lens 108. The imaging power of the ring image i1 is set to be larger than that of the ring image i2.

The diaphragm 110 serves as a second diaphragm and is relayed to the neighborhood of the focusing position behind the objective lens 104 by the lenses 111 and 113. The cornea distance measuring system or first optical system 100 is generally telecentric toward the eye side. The diaphragm 124 serves as a first diaphragm and is relayed to the front of the eye E. A conjugate image (real image) 126 is formed in a position 25 mm to 50 mm away forward from the eye E here.

The calculating device 8 calculates a distance L1 between a reference position Y (not shown) and the corneal vertex position 120P on the basis of image heights y1 and y2 of the ring images i1 and i2 each formed on the two-dimensional sensor 107.

The eye fundus measuring optical system 101 includes a laser source 2, a lens 131, a pin hole 132, a beam splitter 133, a lens 134, a focusing lens 135, a total reflection mirror 136, a lens 137, total reflection mirrors 138, 139, and 140, a lens 148, a reference mirror 5, a total reflection mirror 142, a pin hole 143, a lens 144, and a point-apertured photosensor 145. The laser source 2 is of a short coherent length. The coherent length is, for example, approximately 0.05 mm to 1 mm. The wavelength is near infrared and has an effect for preventing dazzling.

A laser beam emitted from the laser source 2 is condensed to the pin hole 132 by the lens 131. The pin hole 132 serves as a secondary point-like light source.

A laser beam transmitted through the pin hole 132 is split into a light beam proceeding to the lens 134 and another light beam proceeding to the lens 137 by the beam splitter 133. The lens 134 constitutes a measuring optical path 130′ together with the lens 135, the total reflection mirror 136, and the dichroic mirror 115. The other lens 137 constitutes a reference optical path 140′ together with the total reflection mirrors 138, 139 and 140, the lens 148, and the reference mirror 5.

Each of the lenses 134 and 137 serves to collimate the laser beam transmitted through the pin hole 132. The laser beam collimated by the lens 134 is caused to form a spot at a focusing position 146 by the focusing lens 135. This focusing position 146 is conjugate with the eye fundus 147 with respect to the objective lens 104. The laser beam for forming a spot at the focusing position 146 is guided to the eye E via the total reflection mirror 136, the dichroic mirror 115, and the objective lens 104, and forms a spot on the fundus 147. Since the fundus 147 and the focusing position 146 are conjugate with each other with respect to the objective lens 104 in this embodiment, even if the optical axis (optical axis 0 of the objective lens) of the measuring instrument is not coaxial with an optical axis of the eye E, reflected light from the fundus 147 forms an image at the focusing position 146.

The pin hole 143 is disposed at the focusing position of the lens 134 and is conjugate with the fundus 147. The lens 135 serves to collimate the reflected light from the fundus 147 and such collimated light is relayed to the pin hole 143 via the beam splitter 133 and the total reflection mirror 142 by the lens 134. The pin hole 143 becomes conjugate with the pin hole 132 with respect to a reflecting surface of the beam splitter 133. Further, since the pin hole 132 and the spot light 147 on the fundus are conjugate with each other, even if the alignment of the measuring instrument is slightly deviated with respect to the eye E, the reflected light from the fundus 147 can pass through the pin hole 143.

The laser beam collimated by the lens 137 is guided to the reference mirror 5 by the mirrors 138, 139 and 140 and a lens 148. The reference mirror 5 is movable so that the optical path length of the reference optical path and the optical path length of the measuring optical path become the same. The lens 148 is movable together with the reference mirror 5.

The reflected light from the fundus and the reference light are condensed to the pin hole 143, and the light beam transmitted through the pin hole 143 is converged to a photosensor 145 as a first light receiving portion by the lens 144.

As the reference mirror 5 is moved, the difference in optical length between the reference optical path and the measuring optical path is changed. The output from the photosensor 145 is changed like a sine wave every time the difference in optical length is changed by the wavelength. When the difference in optical length is zero, the output of the photosensor 145 is maximum. From the position of the reference mirror 5 corresponding to the maximum output, the calculating device 8 calculates the difference L2 between the reference position Y and the position of the fundus. The position of the reference mirror 5 is detected by a position detecting means (not shown).

The calculating device 8 further subtracts the difference L1 from the difference L2 to obtain the length of the eye axis.

The light receiving portion 7 shown in FIG. 2 includes the two-dimensional image sensor 107 and the photosensor 145 each shown in FIG. 3. The light projecting optical system 3 shown in FIG. 2 includes the ring-shaped light projecting portion 102 and the respective optical members disposed from the objective lens 104 to the lens 131 each shown in FIG. 3. The interference optical system 6 shown in FIG. 2 includes the cornea distance measuring system 100 and the respective optical members disposed from the objective lens 104 to the lens 144 each shown in FIG. 3.

Referring now to FIG. 1, the reference numeral 11 denotes a transducer (heartbeat detecting means) for outputting a heartbeat signal corresponding to the heartbeat of the patient 12, the reference numeral 13 denotes a vital signal generating circuit for outputting an H-leveled vital signal generated when the heartbeat signal exceeds a given level, and the reference numeral 14 denotes a synchronizing circuit for outputting an L-leveled synchronous signal when a measuring switch 15 is pushed. The synchronizing circuit 14 keeps outputting the synchronous signal until the following vital signal is output. The transducer could be formed by a kind of sphygmomanometer in which the maximum or minimum blood pressure is detected to generate a heartbeat signal. The reference numeral 16 denotes a timer for outputting an H-leveled actuating signal when a delay time T elapses from a rising point of time of the L-leveled synchronous signal. The delay time T can be optionally determined.

A means for actuating the eye fundus measuring portion 1 is composed of the vital signal generating circuit 13, the synchronizing circuit 14, the measuring switch 15, and the timer 16.

The reference numerals 17 and 18 denote a monitor for displaying the vital signal and the actuating signal, and a monitor for displaying both interference fringes received by the light receiving portion and a measured result of the eye axis length.

The operation of the instrument will now be described hereinafter.

The light projecting optical system 3 is first aligned by an aligning optical system (not shown) and is focused on the retina of the eye E. The reference mirror 5 is then moved back and forth and is fixed at a position where an output of the photosensor 145 is maximum.

After the transducer 11 is actuated, a heartbeat signal S1 corresponding to the strength of the heartbeat of the patient 12 is output as shown in FIG. 4-a. When the heartbeat signal S1 exceeds a given level, the vital signal generating circuit 13 outputs an H-leveled vital signal S2 (see FIG. 4-b). This vital signal S2 is displayed on the monitor 17. Observing the vital signal S2, the operator sets a delay time T of the timer 16 and determines a phase at the measuring point of time.

Next, the measuring switch 15 outputs an H-leveled switch signal S3 by pushing the measuring switch 15. In response to the switch signal S3, the synchronizing circuit 14 keeps outputting an L-leveled synchronous signal S4. When the vital signal generating circuit 13 outputs the following vital signal S2, the synchronizing circuit 14 stops outputting the synchronous signal S4. The timer 16 is then actuated from this stopping point or rising point (t0) of the synchronous signal S4 in order to output an H-leveled actuating signal S5 when the delay time T elapses. In response to the output of the signal S5, the calculating device 8 is actuated to determine the position of the fundus and the corneal vertex position. An eye axis length is calculated from the position of the fundus.

Since the measurement is carried out when the heartbeat signal S1 or vital signal S2 has a phase predetermined by the timer 16 every time the measuring switch 15 is pushed, it is possible to eliminate a measurement error produced by the change of the reflecting surface caused by the heartbeat.

A judgment whether the reflecting surface of the fundus is the sclera, the choroid, the front surface of the retina, or the rear surface thereof is formed by obtaining four positions of the reference mirror 5 where interference fringes are made or where the output of the photosensor 145 is top. Further, accurate measurement of the eye axis length is performed by finding the respective positions of the reference mirror 5 corresponding to, for example, the rising point t1 of time, the peak point t3, any point t2 between t1 and t3, the intermediate point t4, the falling point t5, and any point t6 between the falling point t5 and the following rising point every each phase of the heartbeats.

Not only such laser beams as mentioned above but also ultrasonic waves are available, of course, to the ophthalmic instrument for finding the position of the eye fundus.

Further, another method may be adopted wherein the amount of light of the laser beam and the amplification degree of signals output by the light receiving portion 7 are increased so that all of the reflected light from the fundus can be received even if the light projecting optical system 3 is focused on any of the reflecting surfaces of the fundus, and interference fringes made by receiving the reflected light are analyzed with a software to discriminate the reflecting surface from which the light is reflected and to correct a measured result.

Further, it is possible to measure the thickness of the retina if the delay time T of the timer 16 is predetermined so that interference fringes occur on the front and rear surfaces of the retina. But, before measuring its thickness, the refractive index of the retina must be decided with respect to the wavelength of the laser beam.

Not only the delay time T of the timer 16 as described above but also a waveform extracting circuit may be used to obtain an optional phase. For example, heartbeat information is collected from an electrocardiogram, and then the optional phase is obtained with the waveform extracting circuit for extracting Q-wave, R-wave, or S-wave.

Further, an analysis of an eyeball movement, for example, can be made from the the position of the eye fundus corresponding to each phase of any vital information, such as respiration, except heartbeat, or each phase of any variation caused by a stimulating means (dosage or physical stimulation).

What is claimed is:

1. An ophthalmic instrument comprising:
   a system for locating a position-of the fundus in a patient's eye;
   heartbeat detecting means for outputting a heartbeat signal synchronized to a heartbeat of the patient; and
   means responsive to the heartbeat signal for actuating said system synchronously with the heartbeat signal, such as to prevent fundus position locating errors caused by patient heartbeats.

2. An ophthalmic instrument according to claim 1, wherein said actuating means actuates said system in synchronized phased relation with said heartbeat signal.

3. An ophthalmic instrument comprising:
   a system for locating a position of the fundus in a patient's eye;
   means for outputting a first signal in response to each heartbeat of the patient;
   initiating means for generating a second signal when operation of the system to locate the fundus position is desired; and
   synchronizing means responsive to the first and second signals for generating a third signal in timed relation with each first signal occurring subsequent in time to each generation of the second signal, each third signal initiating operation of the system.

4. An ophthalmic instrument according to claim 3, comprising a monitor for displaying said first signal.

5. An ophthalmic instrument according to claim 3, wherein said synchronizing means includes a timing circuit for delaying the generation of each third signal by an adjustable time interval relative to a leading edge of each first signal occurring subsequent in time to each generation of the second signal.

6. An ophthalmic instrument according to claim 5, comprising a monitor for displaying said first signal.

7. An ophthalmic instrument comprising:
a system for locating a position of the fundus of a patient's eye;
detecting means for outputting a heartbeat signal synchronized to a heartbeat of the patient;
means for generating a first signal while each heartbeat signal exceeds a threshold amplitude;
an initiation switch for generating a second signal when operation of the system to locate the fundus position is desired;
synchronizing means responsive to the first and second signals for generating a third signal having a duration terminated by a leading edge of one of the first signals occurring subsequent to the generation of the second signal; and
means for generating a fourth signal in delayed time relation to a trailing edge of the third signal, the fourth signal initiating operation of the system.

8. An ophthalmic instrument according to claim 7, comprising a monitor for displaying said first signal.

9. An ophthalmic instrument according to claim 7, wherein the means for generating the fourth signal includes a timing circuit for adjustably establishing the delayed time relation between the third and fourth signals.

* * * * *

UNITED STATES PATENT AND TRADEMARK OFFICE
CERTIFICATE OF CORRECTION

PATENT NO. : 5,400,091
DATED : March 21, 1995
INVENTOR(S) : Yasuhiro OKAZAKI

It is certified that error appears in the above-indentified patent and that said Letters Patent is hereby corrected as shown below:

Title page:
Attorney, Agent, or Firm, Title Page , Line 1, after "Henderson" insert --,--.

Claim 1, Column 6, Line 34 "position-of" should read --position of--.

Signed and Sealed this

Thirteenth Day of June, 1995

Attest:

BRUCE LEHMAN

Attesting Officer            Commissioner of Patents and Trademarks